United States Patent [19]

Hovatter

[11] Patent Number: 5,683,659
[45] Date of Patent: Nov. 4, 1997

[54] INTEGRAL ASSEMBLY OF MICROCENTRIFUGE STRIP TUBES AND STRIP CAPS

[76] Inventor: Kenneth R. Hovatter, 1901 Ackerman Dr., Lodi, Calif. 95240

[21] Appl. No.: 680,227

[22] Filed: Jul. 11, 1996

Related U.S. Application Data

[63] Continuation of Ser. No. 392,346, Feb. 22, 1995, abandoned.

[51] Int. Cl.$^6$ .................................................. G01N 21/03
[52] U.S. Cl. .................. 422/102; 422/58; 422/72; 422/99; 422/101; 220/336; 220/339; 220/375
[58] Field of Search .............................. 422/99, 101, 102, 422/58, 72; 220/82 R, 307, 336, 339, 375; D24/223, 226, 227, 225

[56] References Cited

U.S. PATENT DOCUMENTS

| | | | |
|---|---|---|---|
| D. 226,846 | 5/1973 | Rosenburg | D16/1 |
| D. 269,702 | 7/1983 | Suovaniemi et al. | D24/8 |
| D. 271,619 | 11/1983 | Herrmann | D24/29 |
| D. 288,845 | 3/1987 | Borer et al. | D24/29 |
| D. 321,940 | 11/1991 | D'Aquino et al. | D24/226 |
| D. 325,638 | 4/1992 | Sloat et al. | D24/226 |
| D. 332,145 | 12/1992 | Wada et al. | D24/227 |
| 4,348,207 | 9/1982 | Cappel | 422/102 X |
| 4,639,135 | 1/1987 | Borer et al. | 356/246 |
| 4,671,939 | 6/1987 | Mintz | 422/58 |
| 4,713,219 | 12/1987 | Gerken et al. | 422/102 |
| 4,755,356 | 7/1988 | Robbins et al. | 422/102 |
| 4,948,564 | 8/1990 | Root et al. | 422/101 |
| 5,005,721 | 4/1991 | Jordan | 220/23.4 |
| 5,110,556 | 5/1992 | Lyman et al. | 422/101 |
| 5,254,314 | 10/1993 | Yu et al. | 422/102 |
| 5,270,011 | 12/1993 | Altherr | 422/102 |

FOREIGN PATENT DOCUMENTS 2056743  5/1992  Canada.

*Primary Examiner*—Harold Pyon
*Attorney, Agent, or Firm*—John J. Leavitt; George M. Cooper; William A. Blake

[57] ABSTRACT

Presented is an integral assembly (2) of hollow tubes and seal caps (4) therefor arranged in an elongated aligned and integral assembly in which multiple tubes (1) each symmetrical about a longitudinal axis (3) and having a closed (32) end and an open end (6) are formed in side-by-side spaced relationship in a linear series in which adjacent tubes are integrally interconnected by a tether (36) to form an elongated strip (2). One end of the strip (2) of open-ended tubes is integrally connected to an elongated seal cap strip (43) that forms an integral extension of the tube strip and which includes a linear series of integral, spaced seal caps (42) each symmetrical about an axis (44) parallel to the axes of the tubes and corresponding in spacing and in number to the tubes. The tube (1) on one end of the tube strip (2) is integrally connected to its corresponding seal cap (42) on the seal cap strip (43). A hinge (41) is provided integrally interposed between the tube strip and the cap strip so that when the cap strip is manipulated into superimposed relationship over the tube strip, the axes of the seal caps coincide with the axes of the tubes and the seal caps of the cap strip may be pressed to sealingly engage the open ends of the tubes of the tube strip.

13 Claims, 3 Drawing Sheets

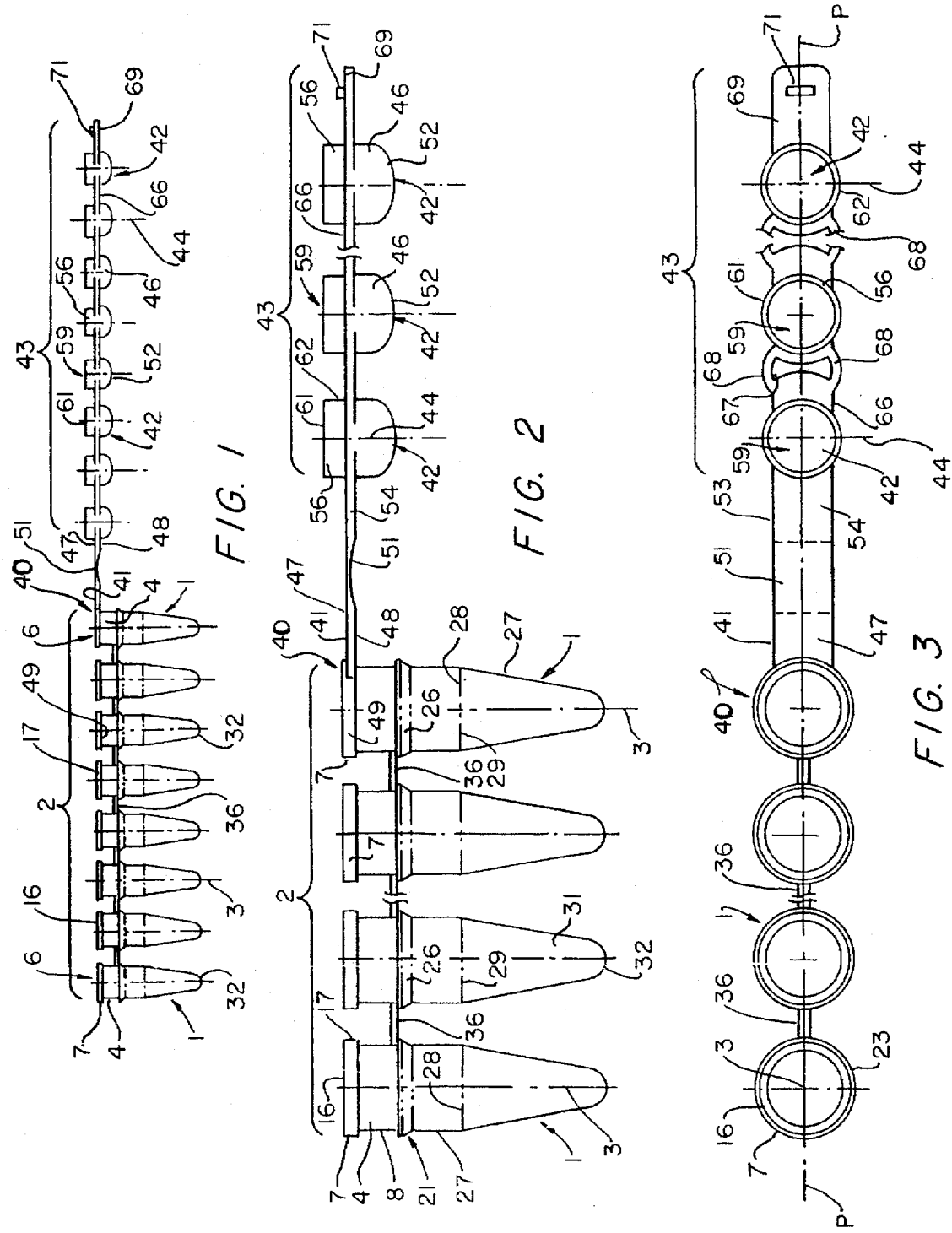

INTEGRAL ASSEMBLY OF MICROCENTRIFUGE STRIP TUBES AND STRIP CAPS

This application is a continuation of copending application(s) Ser. No. 08/392,346 filed on Feb. 22, 1995 now abandoned.

BACKGROUND OF THE INVENTION

1. Field of the Invention

This invention relates to hollow strip tubes closed at one end and open at the opposite end and strip caps for selectively sealing and unsealing the open ends of the tubes, such as microcentrifuge tubes, for instance, and more particularly to an integral assembly of such strip tubes and strip caps arranged in an integral cooperative unitary assembly in both tube-sealed and tube-unsealed condition.

2. Description of the Prior Art

A preliminary patentability and novelty search in connection with this invention has revealed the existence of the following United States patents:

| | | |
|---|---|---|
| D-288,845 | D-271,619 | D-269,702 |
| D-332,145 | D-226,846 | D-325,638 |
| D-321,940 | D-316,449 | 4,675,299 |
| 4,671,939 | 4,472,357 | 4,639,135 |
| 3,905,772 | 4,648,713 | 5,005,721 |
| | 5,110,556 | |

A careful review of these patents has failed to disclose or suggest the concept of, or disclose or suggest a structural assembly of, multiple integrally connected hollow strip tubes serially arranged in a predetermined pattern and integrally connected to a complementary elongated strip of integrally connected caps for selectively sealing the tubes when the caps are superimposed over the tubes. It is particularly advantageous in the handling of reagent-containing vials or tubes, such as microcentrifuge tubes, that the tubes and the caps for sealing the tubes constitute a unitary assembly. Accordingly, it is one of the objects of the present invention to provide a unitary assembly of multiple hollow tubes integrally connected to one another and to a corresponding number and placement of seal caps for the tubes so that the integral assembly of tubes and caps may be handled as a unit.

Another object of the invention is the provision of a unitary assembly of tubes and caps integrally connected and arranged serially in patterns that complement one another when the caps are superimposed on the tubes.

A still further object of the invention is the provision of a unitary assembly of tubes and caps integrally connected and arranged serially in a straight line wherein the elongated strip of multiple caps constitutes an integral extension of the elongated strip of hollow tubes in the un-sealed condition of the tubes and caps.

Yet another object of the invention is the provision of an elongated strip comprised of spaced integrally connected hollow tubes integrally connected at one of its ends to an associated end of an elongated strip comprised of correspondingly spaced integrally connected seal caps in a manner that the strip of seal caps may be brought into superimposed sealing relationship with the strip of tubes.

A still further object of the invention is the provision of an integral assembly of a strip of hollow tubes having open ends and a strip of seal caps adapted to seal the open ends of the tubes when brought into superimposed relationship therewith wherein the strip of caps in un-sealed condition constitutes an integral linearly aligned extension of the strip of tubes, and an integral "live" hinge is integrally interposed between the associated ends of the tube strip and the cap strip enabling flexible manipulation of the cap strip at the hinge from a linearly aligned integral extension condition to an integral superimposed tube-sealing condition.

The invention possesses other objects and features of advantage, some of which, with the foregoing, will be apparent from the following description and the drawings. It is to be understood however that the invention is not limited to the embodiment illustrated and described since it may be embodied in various forms within the scope of the appended claims.

SUMMARY OF THE INVENTION

In terms of broad inclusion, the integral assembly of hollow tubes and seal caps therefor comprises an elongated assembly in which multiple tubes each symmetrical about a longitudinal axis and having a closed end and an open end are formed in side-by-side spaced relationship in a linear series in which adjacent tubes are integrally interconnected to form an elongated strip. One end of the strip of open-ended tubes is integrally connected to an elongated cap strip that constitutes an integral extension of the tube strip and which includes a linear series of integral spaced seal caps each symmetrical about an axis parallel to the axis of the tubes and corresponding in spacing and in number to the tubes. The tube on one end of the tube strip is integrally connected to its corresponding seal cap on the cap strip, and the spacing between this end tube and its associated seal cap is greater than the spacing between the tubes of the tube strip and greater than the spacing between the remaining caps in the cap strip. A hinge means is provided integrally interposed between the tube strip and the cap strip whereby when the cap strip is manipulated into superimposed relationship to the tube strip, the axes of the seal caps coincide with the axes of the tubes and the seal caps of the cap strip sealingly engage the open ends of the tubes of the tube strip.

BRIEF DESCRIPTION OF THE DRAWINGS

FIG. 1 is a side elevational view shown actual size the complete assembly of integral strip tubes and integral strip caps shown in tube-open condition.

FIG. 2 is a side elevational view of the complete assembly shown greatly enlarged for clarity and shown in tube-open condition, with intermediate sections of the tube strip and cap strip broken away to shorten the length of the view.

FIG. 3 is a top plan view of the complete assembly shown greatly enlarged for clarity and shown in tube-open condition, with intermediate sections of the tube strip and cap strip broken away to shorten the length of the view.

DESCRIPTION OF THE PREFERRED EMBODIMENT

Figure 4:
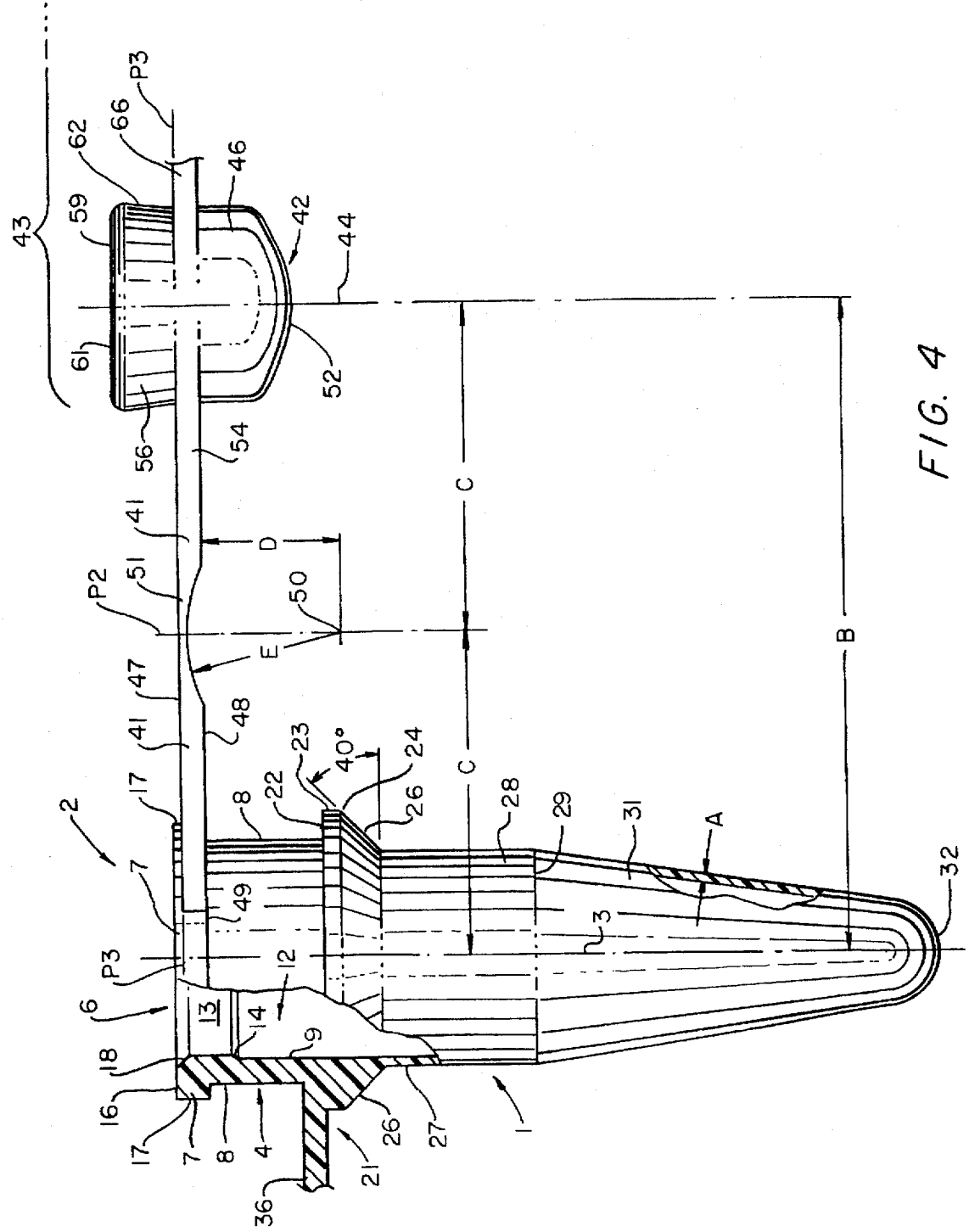
FIG. 4 is a fragmentary side elevational view illustrating the manner of flexible integral interconnection of the tube strip to the cap strip. The view is shown greatly enlarged for clarity, and a portion of the tube structure is shown in cross-section.

In terms of greater detail, the integral assembly of microcentrifuge strip tubes and strip caps facilitates all of the functions involved in the handling and use of such tubes, and therefore saves time, resulting in increased efficiency and greater production. The importance of the integrality of the assembly with respect to facilitating handling will be readily apparent when it is understood that the overall length of each tube is less than one inch, while the inner diameter of the open end of each tube is less than one quarter inch. It is difficult to digitally manipulate such a small individual tube, and it is has been found that connecting multiple such tubes into an integral assembly, including the seal caps, greatly facilitates handling.

Structurally, the integral assembly comprises a multiplicity, say eight or more, of microcentrifuge tubes, each tube designated generally by the numeral 1, and the integral assembly of multiple tubes designated generally as an assembly by the numeral 2. Each of the tubes is hollow and symmetrical about a central axis 3, is identical to each of the other tubes, and includes an upper cylindrical relatively thick-walled body portion 4 defined by an open end 6. Exteriorly, the open end of each tube is surrounded by an integral concentric first collar 7 constituting a circular flange projecting radially outwardly from and integral with the cylindrical outer surface 8 of the thick-walled body portion 4. As shown in the drawings, the collar 7 forms a relatively narrow 0.040" wide band about the open end of the associated tube. A sense of the small and delicate nature of the tube structure is derived when it is understood that the remainder of the thick-walled cylindrical body portion 4 is only 0.100" long measured parallel to the central axis of the tube.

Interiorly, again referring to the thick-walled portion of the tube associated with the open end thereof, the inner peripheral concentric surface 9 of the thick-walled body portion 4 is provided adjacent the open end 6 of the tube with a radially inwardly projecting integral concentric bead designated generally by the numeral 12, and including a cylindrical flat inner surface 13 defined by a lower beveled surface 14. It is important to note that the beveled surface 14 rises integrally from the inner surface 9 at an angle of 30 degrees. At its open end, each tube is provided with a flat annular top surface 16 the outer periphery of which is coincident with and intercepted by the outer periphery 17 of the collar 7. The inner periphery of the annular top surface 16 is defined by the base of an inverted truncated conical surface 18 that intercepts the cylindrical flat surface 13 at an angle of 45 degrees coincident with a plane spaced from and parallel with the annular flat surface 16 of the open end of the tube. These relationships are important because they interrelate in a functionally cooperative manner with the means by which each of the tubes is sealed, as will hereinafter appear.

Spaced axially from the open end 6 of the tube, and formed integrally with the thick-walled body portion 4, and spaced axially below the collar 7, and extending radially outwardly from the outer surface 8 of the body portion 4, there is provided a concentric second collar or circumscribing shoulder designated generally by the numeral 21, and including an upper flat annular surface 22 intercepted by a cylindrical surface 23, which in turn, at its lower end 24, is intercepted by a conical surface 26 tapered at 40 degrees to the horizontal and which merges smoothly and integrally with the outer surface 27 of a relatively thin-wall section 28 of the tube, as shown in the FIGS. 4 and 5. The conical surfaces 26 form shoulders for supporting the integral tube assembly in an appropriate aperture formed in a support plate (not shown). The thin-walled section 28 of the tube is tapered inwardly by about one degree for a length of about 0.165", terminating in an integral union at 29 with a more sharply inwardly tapered wall portion 31 that culminates in a generally rounded closed end 32 as illustrated in the drawings. The more sharply tapered wall portion 31 tapers at an angle of about 8.5 degrees with the central axis of the tube.

Each of the tubes thus formed is integrally connected to the adjacent tube to form an integral linear array or series of tubes as illustrated in FIGS. 1, 2 and 3, that are collectively arranged symmetrically so that their axes are parallel and contained in a common plane P that bisects the tubes.

The integral connection between adjacent tubes is formed by a strap or tether 36 that is also bisected by the common plane P that contains the longitudnal axes of the tubes. Since the linear series of eight tubes from center-to-center of the end tubes is only about 2.5 inches, it will be appreciated that each tether or strap 36 is less than 0.10" in length and approximately one half that amount in width. Since the tethers are all the same length, and since the tubes are all the same diameter, it follows that the longitudinal axes 3 of the adjacent tubes are equally spaced one from the other, this spacing being about 0.354 inches.

As illustrated in the drawings, the end tube at one end 40 of the integral and linear assembly of tubes is integrally connected by a flexible hinge strap designated generally by the numeral 41 to an integral and linear assembly of seal caps, each cap being designated generally by the numeral 42, while the linear assembly of integrally connected seal caps is designated generally by the numeral 43. As shown, there are as many seal caps as there are tubes, and each seal cap is symmetrical about a central axis 44. In the tube-open or extended arrangement illustrated in FIGS. 1 and 2, the central axes of the tubes and the central axes of the seal caps are parallel and collectively contained or coincident with the plane P that bisects both the tubes and the seal caps.

As illustrated in the drawings, the hinge strap 41 at one end merges integrally with the collar 7 of the associated end tube 1 positioned at the end 40 of the integral linear assembly of tubes. At its opposite end, the hinge strap 41 merges integrally with the side wall 46 of the associated end seal cap 42 of the integral series of end caps 43. It should be noted that the flexible hinge strap, the integrally connected tubes, and the integrally connected seal caps are all preferably formed as a single unitary structure by injection molding from a suitable synthetic resinous material. It is also important to note that the thickness of the flexible hinge strap measured between its upper surface 47 and its lower surface 48 is less than the width of the collar 7, and that the lower surface 48 is flush with the lower surface 49 of the collar 7.

Medianly between the axis 3 of the end tube connected to the flexible hinge strap and the axis 44 of the end seal cap connected to the opposite end of the flexible hinge strap, the hinge strap is thinned in thickness in a portion 51. Preferably, the thinned portion 51 is arcuate about a point 50 spaced below the hinge strap and coincident with a plane P2 that bisects the distance between the axis 3 of the associated end tube and the axis 44 of the associated end seal cap. The plane P2 is perpendicular to the plane P that is coincident with the axes 3 of the linearly arranged tubes. The radius of curvature of the arcuate portion 51 is conveniently sufficient to reduce the thickness of the portion 51 to about 0.019 inches measured where the plane P2 extended intersects the hinge strap. The thinned portion 51 thus constitutes a so-called "live" hinge about which the assembly of integrally connected and serially arranged seal caps may be pivoted to bring each of the seal caps into a superimposed relationship with a correspondingly positioned tube as illustrated in the drawings. By "live" hinge, it is meant that the thin hinge portion is integral with the remainder of the strap with which it is integrally formed yet is so flexible that it will readily flex so that the strap portions on opposite side of the "live" hinge lie superimposed one above the other in parallelism.

Figure 5:
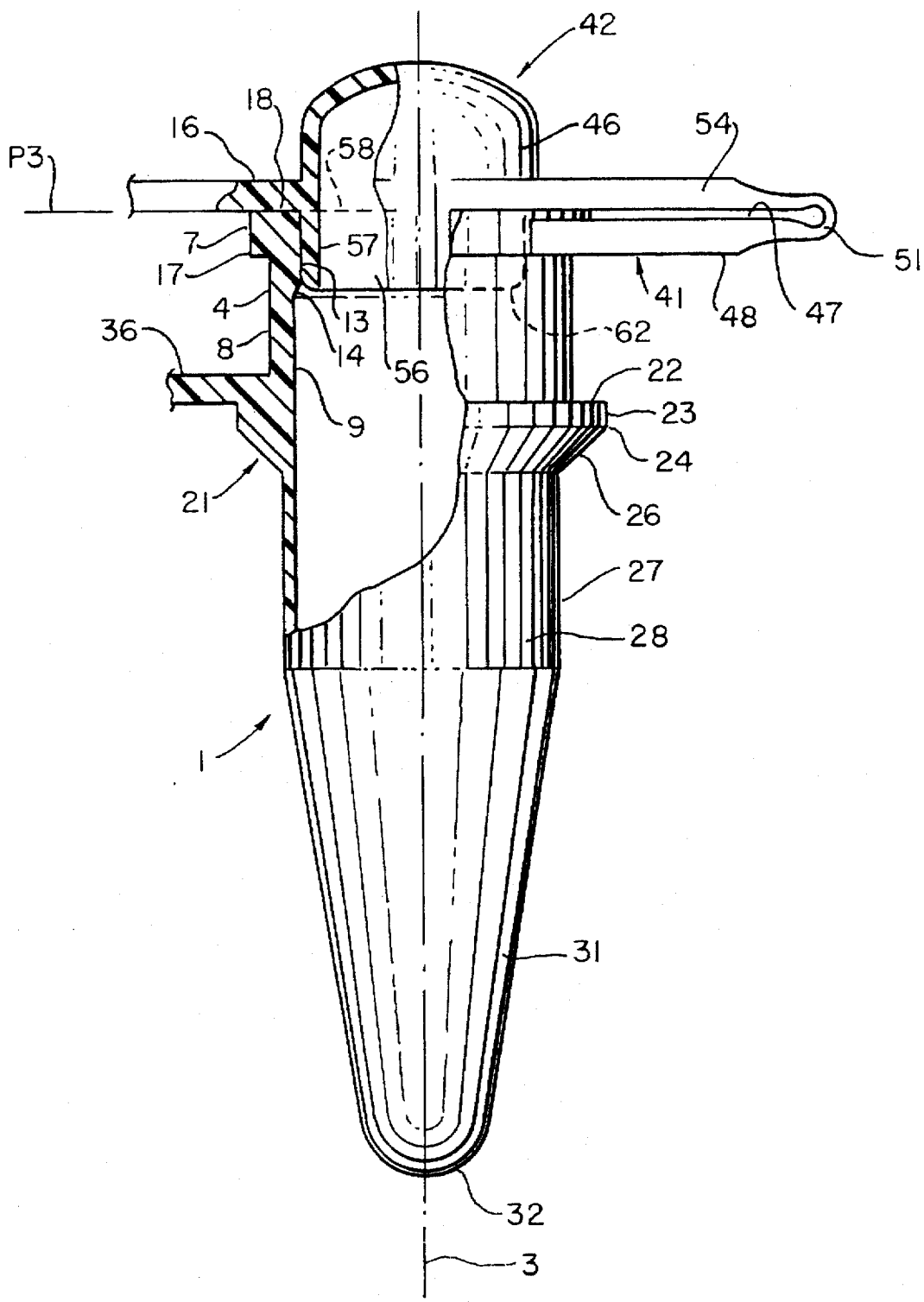
FIG. 5 is a fragmentary elevational view illustrating the flexible integral hinge means integrally interconnecting the tube strip to the cap strip folded over to effect sealing superimposition of one of the cap structures within the open end of the adjacent tube structure. The view is shown greatly enlarged for clarity and a portion of both the tube and seal cap are broken away to reveal the sealing engagement of the seal cap with the tube.

To effect a seal between each of the individual seal caps and its associated tube, it is important to note from FIG. 5 of the drawings that each seal cap is provided with a spherically configured end wall 52 that is intercepted circumferentially by cylindrical wall portion 46, the diameter of the outside surface of which is substantially equal to the width of the hinge strap 41 so that the longitudinal edges 53 and 54 extend substantially tangentially from the cylindrical wall portion 46.

Again as illustrated in FIG. 5, it will be seen that on the opposite side of the hinge strap from the spherical end wall 52 and the cylindrical wall portion 46, each seal cap is provided with a skirt portion 56 the inner surface 57 of which tapers radially outwardly from a point 58 that is coincident with a plane P3 that is coincident with the surface 47 of the hinge strap for the end seal cap integrally connected to the hinge strap. The skirt terminates in an open end 59 defined by the end edge 61 that intercepts the inner outwardly tapered surface 57 and which merges smoothly with the outer surface 62 of the skirt portion, which is also tapered outwardly commencing at the surface 47 of the hinge strap.

Thus, by virtue of the tapered configuration of the skirt portion, the diameter of end edge 61 of the skirt portion that defines the open end 59 of the seal cap is somewhat larger than the inner diameter of the cylindrical surface 13 formed on the inner periphery of each of the tubes. Stated in other words, the outer diameter of the open end of each seal cap is related to the inner diameter of the open end of each associated tube in a manner so that when a seal cap is superimposed over the open end of a tube, the radiused outer end surface of the open end of the seal cap impinges on the inwardly tapered conical surface 18 of the tube. Pressure applied on the spherical end wall of the seal cap causes a camming action to occur between these two surfaces that results ultimately in the skirt portion being elastically compressed radially inwardly until a sealing press-fit occurs between the outer flared surface 62 of the skirt portion and the cylindrical inner surface 13 of the tube. When each seal cap is fully sealingly engaged as shown in the drawings in the open end of an associated tube, the length of the skirt portion of the seal cap and the depth of the seal surface 13 within the tube are such that the end edge 61 of the skirt portion lies confined within the limits of the cylindrical seal surface.

Referring to the drawings, it will be seen that in the seal cap assembly 43, adjacent seal caps are integrally attached to one another by an integral web designated by the numeral 66. Each web, at opposite ends, is integral with the associated seal cap and, collectively, the webs lie in a common plane that includes the flexible hinge strap 61. Additionally, each web possesses a width that is approximately equal to the diameter of the seal cap at the plane of attachment. For purposes of flexibility, each web 66 is formed with a centrally disposed aperture 67 as shown, having a generally hour-glass configuration that extends transversely across the web to define arcuate edge portions 68 along opposite edges of the web. Flexibility of the web between adjacent seal caps is thus enhanced, facilitating registry of each seal cap with a corresponding tube.

To complete the seal cap assembly 43, there is provided attached to the last tube in the assembly remote from the hinge strap 61, an integral tab 69 having a lug 71 projecting therefrom to facilitate grasping the tab 69 to effect opening of the tubes by detachment of the seal caps therefrom. The tab is conveniently the same width as the web portions 66 integrally attached to the seal cap walls.

Having thus described the invention, what is believed to be new and novel and sought to be protected by letters patent of the United States is as follows.

I claim:

1. A unitary assembly of microcentrifuge tubes and caps formed from a single piece of synthetic resinous material, said assembly comprising:
    a) a plurality of spaced, microcentrifuge reagent tubes arranged in an elongated aligned series, each tube having an open end, a closed end and an external support collar positioned between said open end and said closed end;
    b) a plurality of tether means for interconnecting said plurality of microcentrifuge reagent tubes, each of said tether means extending from adjacent ones of said tubes at a position on each of said tubes between said open end and said collar;
    c) a plurality of seal caps arranged in an elongated aligned series;
    d) a plurality of webs for interconnecting said plurality of seal caps, each of said webs interconnecting adjacent ones of said seal caps in a spaced manner so that each of said seal caps can be engaged with an open end of a corresponding one of said reagent tubes; and
    e) a flexible hinge strap connecting an end one of said reagent tubes to an end one of said seal caps, said hinge strap including a live hinge portion for enabling said plurality of seal caps to pivot into engagement with the open ends of corresponding ones of said reagent tubes, wherein said each of said microcentrifuge reagent tubes has a length of less than one inch.

2. The assembly of claim 1, wherein each of said tether means extends from adjacent ones of said tubes at a position on each of said tubes adjacent a top edge of said collar.

3. The assembly according to claim 1, wherein the open ends of said reagent tubes lie in a common plane.

4. The assembly according to claim 1, wherein said plurality of tether means interconnecting said plurality of reagent tubes are coincident in a common plane.

5. The assembly according to claim 1, wherein said each of said webs interconnecting adjacent ones of said seal caps in a spaced manner is provided with an aperture therein extending transverse to the web and defining flexible peripheral strap members disposed between adjacent seal caps, whereby said webs between adjacent seal caps accommodate flexure between said seal caps to facilitate sealing engagement and disengagement of said series of seal caps with said series of reagent tubes.

6. The assembly according to claim 1, wherein each of said seal caps is provided with an open and a closed end, and said webs interconnecting said elongated aligned series of seal caps are connected to said seal caps in a plane coincident with the plane of said hinge strap, whereby in the extended aligned position of said integrally connected seal caps said open ends of said seal caps lie in a plane parallel and spaced from a plane including the open ends of said reagent tubes, while the closed ends of said seal caps lie in a plane parallel and spaced on the opposite side of the plane including the open ends of said reagent tubes.

7. The assembly according to claim 1, wherein said plurality of spaced, microcentrifuge reagent tubes are each symmetrical about a central axis and arranged in an uninterrupted strip in which the axes of the plurality of tubes are parallel to one another, equally spaced apart, and coincident with a common plane, and each seal cap is symmetrical about a central axis parallel to the axes of the remaining seal caps and includes a closed end, an open end, and a tapered skirt portion adapted to selectively sealingly engage the open end of an associated reagent tube.

8. The assembly according to claim 7, wherein said hinge strap is approximately twice the length of the spacing between the axes of two adjacent reagent tubes, and includes opposite long edges that are substantially tangent to the periphery of said end one of said seal caps to which the hinge strap is connected.

9. The assembly according to claim 7, wherein the outside diameter of said open end of said tapered skirt portion on each seal cap is greater than the inner diameter of the open end of the reagent tube, whereby when a seal skirt portion is pressed into the open end of an associated reagent tube, the differential in diameters effects elastic compression of said skirt portion to seal the open end of the associated reagent tube.

10. The assembly according to claim 1, wherein each of said reagent tubes is elongated in the direction of its central axis and includes a cylindrical body portion adjacent its open end, a circular flange disposed integrally about said cylindrical body portion and defining the open end of said reagent tube, said external support collar being disposed integrally about said cylindrical body portion and spaced axially from said circular flange, and a cylindrical seal surface within the open end of each reagent tube concentrically disposed in relation to said circular flange and adapted to elastically sealingly compress an associated seal cap when said seal cap is pressed into the open end of the associated reagent tube.

11. The assembly according to claim 10, wherein said flexible hinge strap integrally connects the circular flange on said end one of said reagent tubes to an end one of said seal caps medianly between opposite ends thereof.

12. The assembly according to claim 10, wherein each said reagent tube includes a first conical wall portion connected at one end to said support collar and extending toward the closed end of the reagent tube, and a second conical wall portion integral with said first conical wall portion at one end and closed at its opposite end.

13. The assembly according to claim 10, wherein said cylindrical body portion of each reagent tube includes a cylindrical inner peripheral surface, said cylindrical seal surface is spaced radially inwardly and concentrically with respect to said cylindrical inner peripheral surface, and a beveled surface is provided intercepting said cylindrical seal surface and the open end of the reagent tube, whereby said skirt portion of an associated seal cap is cammed into elastic compression when sealingly inserted into said cylindrical seal surface.

* * * * *